United States Patent [19]

Coates et al.

[11] Patent Number: 5,312,563
[45] Date of Patent: May 17, 1994

[54] FLUORINATED 4"-CYANO SUBSTITUTED TERPHENYLS

[75] Inventors: David Coates, Wimbourne; Ian Sage; Simon Greenfield, both of Dorset; George W. Gray, North Humberside; David Lacey, North Humberside; Kenneth J. Toyne, North Humberside; Lawrence K. Chan, Middlesex; Michael Hird, North Humberside, all of England

[73] Assignee: The Secretary of State for Defence in her Britannic Majesty's Government of the U.K. of Great Britain and Northern Ireland, London, England

[21] Appl. No.: 7,821

[22] Filed: Jan. 22, 1993

Related U.S. Application Data

[63] Continuation of Ser. No. 659,351, Feb. 19, 1991, abandoned.

[30] Foreign Application Priority Data

Jun. 16, 1988 [GB] United Kingdom ............... 8814327

[51] Int. Cl.⁵ ............... C09K 19/12; C09K 19/52; C07C 25/13
[52] U.S. Cl. .................. 252/299.66; 570/127; 252/299.01

[58] Field of Search .............. 252/299.01, 299.66, 252/299.65, 299.63, 299.61; 570/127

[56] References Cited

U.S. PATENT DOCUMENTS

| | | | |
|---|---|---|---|
| 3,974,087 | 8/1976 | Gray et al. | 252/299 |
| 4,077,260 | 3/1978 | Gray et al. | 252/299 |
| 4,696,549 | 9/1987 | Chan et al. | 252/299.66 |
| 4,818,428 | 4/1989 | Scheuble et al. | 252/299.1 |
| 4,834,906 | 5/1989 | Coates et al. | 252/299.63 |
| 5,030,383 | 7/1991 | Scheuble et al. | 252/299.61 |

FOREIGN PATENT DOCUMENTS 3906038 2/1989 Fed. Rep. of Germany.

OTHER PUBLICATIONS

Mol. Cry. & Liq. Cry. vol. 158B pp. 209-240. May 1988.

*Primary Examiner*—Shean Wu
*Attorney, Agent, or Firm*—Nixon & Vanderhye

[57] ABSTRACT

Fluorinated 4"-cyano substituted terphenyls of general formula (I), wherein $R_1$ is selected from alkenyl, H, R, RO and RCO where R is alkyl or perfluoroalkyl containing up to 12 carbon atoms, n is 1, 2 or 3 and the lateral fluorosubstituent(s) may be in any of the available substitution positions are provided. These have liquid crystalline properties and may be used as components of liquid crystal materials.

11 Claims, 1 Drawing Sheet

FLUORINATED 4"-CYANO SUBSTITUTED TERPHENYLS

This is a continuation of application Ser. No. 07/659,351, filed Feb. 19, 1991, now abandoned.

This invention relates to novel fluorinated 4"-cyano substituted terphenyls, to novel methods of preparation of such terphenyls, and to liquid crystal materials which incorporate them, in particular liquid crystal materials which show a nematic phase. Such liquid crystal materials may be used industrially as the working fluid of electro-optic display devices.

BACKGROUND OF THE INVENTION

The use in liquid crystal materials of 4-alkyl and 4-alkoxy-4"-cyano terphenyls is described in GB 1433130, among many other publications and liquid crystal materials containing them are widely used. GB1433130 suggests the possibility of one of the three phenyl rings being laterally substituted, suggested substituents being the bulky methyl group or an unspecified halogen. No example of any such laterally substituted terphenyl is disclosed in GB1433130, no method for their preparation is given, and no preference for any particular halogen substituent is expressed.

GB2039937A describes liquid crystal materials which contain at least one laterally substituted 4-alkyl-4"-cyanoterphenyl of general structure:

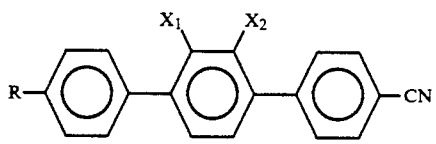

where R is alkyl, one of $X_1$ or $X_2$ being hydrogen and the other being methyl or a halogen preferably the bulky chlorine. A complex 6 step method for preparation of these terphenyls is described in GB2039937A, but no example of a terphenyl having $X_1$, or $X_2$ as a halogen is described, the implication being that none were made.

Mol. Cryst. Liq. Cryst. (1985) 123 169–177 describes 2 and 2' fluorosubstituted 4-alkyl-4'-cyanobiphenyls, but the data presented therein suggests that lateral fluorination increases the melting point of these compounds, and that their solubility in liquid crystal materials is low.

Laterally fluoro-substituted terphenyls of general structure:

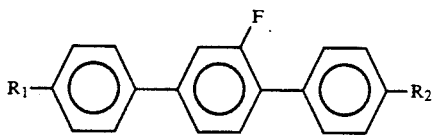

where $R_1$ and $R_2$ are alkyl or alkoxy are known and examples are given in EP-A-0132377. The preparation method described therein cannot easily be applied to the preparation of a terminally cyano substituted terphenyl.

The present invention has identified a class of terphenyls which on the basis of the prior art discussed above appear to be newly prepared and which show advantageous properties. A novel process for their synthesis which for the first time makes them also commercially viable has also been discovered.

DESCRIPTION OF THE INVENTION

Figure 1:
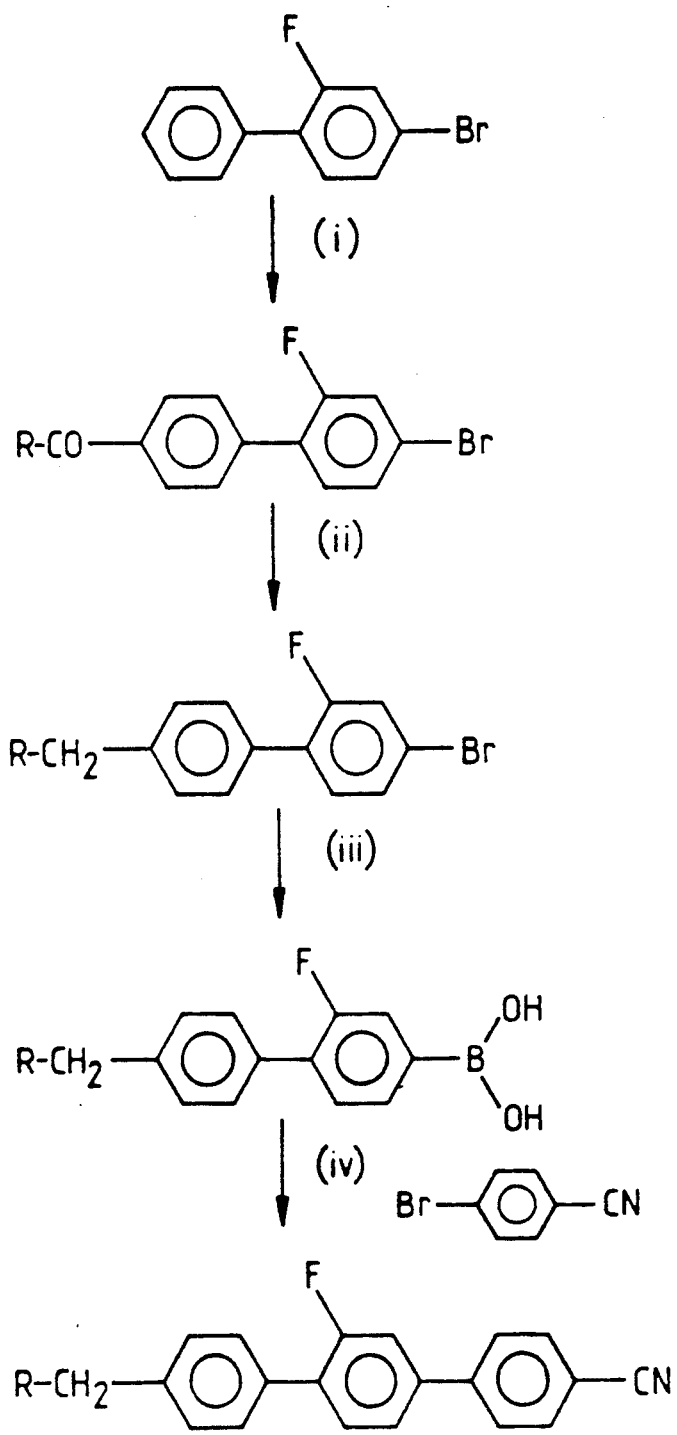
FIG. 1 shows the synthesis of 4-alkyl-2'-fluoro-4"-cyano 1,1':4,4' terphenyl according to Example 1.

According to the present invention, fluorinated 4"-cyano substituted terphenyls are provided, of general formula I:

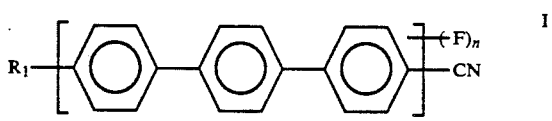

wherein $R_1$ is selected from alkenyl, H, R, RO, and RCO where R is alkyl or perfluoralkyl containing up to 12 carbon atoms, n is 1, 2 or 3 and the lateral fluoro substituent(s) may be in any of the available lateral substitution positions.

The structural preferences expressed below are inter alia on the basis of usefulness or constituents of liquid crystal mixtures and ease of preparation.

The group $R_1$ is preferably alkyl or alkoxy, and may be straight chain (n), branched (iso) or may contain an asymmetrically substituted carbon atom so as to be a chiral group. When $R_1$ is organic it preferably contains from 2 to 9 carbon atoms, especially from 2 to 7. Particularly useful compounds are those in which $R_1$ is n-alkyl or n-alkoxy, or the chiral groups (+) or (−) 2-methylbutyl, 2-methylbutyloxy, 3-methylpentyl, 3-methylpentyloxy, 4-methylhexyl or 4-methylhexyloxy.

Preferably n is 1 or 2, and preferred structures for the terphenyl of formula I are those having fluoro substituents in the positions listed below in table 1, in which the nomenclature:

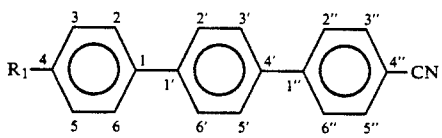

is used for the lateral substitution positions.

TABLE 1

2'-fluoro-
3'-fluoro-
3"-fluoro-
2"-fluoro
2-fluoro
3-fluoro
2, 3"-difluoro
3, 3"-difluoro
3, 2"-difluoro
2, 2"-difluoro
3, 3'-difluoro
3, 2'-difluoro
2, 2'-difluoro
2, 3'-difluoro
3', 2"-difluoro
2',3"-difluoro
3', 3"-difluoro
2', 2"-difluoro
3,5-difluoro
2,6-difluoro
2,5-difluoro 3',5'-difluoro
2',6'-difluoro
2',5'-difluoro
3",5"-difluoro
2",6"-difluoro
2",5"-difluoro
2,3-difluoro
2',3'-difluoro
2",3"-difluoro Of these, 4-alkyl or alkoxy, 2'-fluoro, 3"-fluoro, 2-fluoro, 3'-fluoro, 2', 3"-difluoro, 2, 3"-difluoro, and 3", 5"-difluoro substituted compounds of formula I are particularly preferred, especially 2'-fluoro compounds.

A suitable method for the preparation of a compound of formula I as defined above is one in which a boronic acid of formula II:

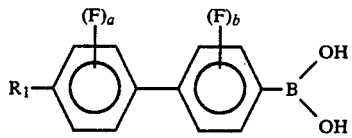

wherein R₁ is as defined in formula I, a and b are 0,1,2 or 3 is coupled with a benzonitrile of formula III:

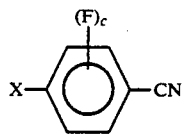

wherein X is chlorine, bromine or iodine, c is 0,1,2 or 3, provided (a+b+c) is 1,2 or 3, to form the compound of formula I.

In this method coupling occurs between the ring positions to which the B(OH)₂ and X groups are attached. The indicated fluorine substituent(s) (F) may be in any of the available substitution positions. Preferably (a+b+c) is 1 or 2 and these are one or two fluorine substituents in the compounds of formulae II and III are preferably disposed so as to form compounds of formula I as listed in table I, and suitable fluoro substitution patterns for compounds of formulae II and III will be apparent to those skilled in the art.

Boronic acids II may be prepared starting from known biphenyls IV:

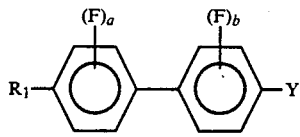

wherein Y is chlorine, bromine or iodine, preferably bromine. Biphenyls IV in which R₁ is hydrogen may be converted into those which R₁ is R or RCO by means of a Friedel-Crafts reaction using an acyl chloride RCOCl to add a group RCO at the available 4-position, which may then be reduced to an alkyl group using for example hydrazine hydrate, or a trialkyl silane, triethyl silane being preferred.

To prepare the boronic acid II, the biphenyl IV is preferably first converted into a Grignard reagent by reaction of the biphenyl IV with magnesium metal in for example an ether such as tetrahydrofuran (THF). Conditions for preparation of Grignard reagents are well known.

The Grignard reagent may then be reacted with a trialkyl borate (R'O)₃B, where R' is alkyl, preferably methyl or isopropyl, conveniently in the same solvent in which the Grignard reagent was prepared. The resulting boronated product is then hydrolysed, for example with a mineral acid, preferably hydrochloric acid. The compound II may then be isolated and purified conventionally. Some methods for preparation of unfluorinated, monofluorinated and difluorinated biphenyls of formula IV are described in detail in WO 89/02425 and PCT/GB 88/00880.

Benzonitriles of formula III are known and are available commercially or may be synthesised, e.g. as described in GB 8804330 A or PCT/GB 89/00178. Preferably X is bromine. The coupling step is preferably carried out in the presence of a coupling agent, such as a palladium (O) catalyst, preferably tetrakis (triphenylphosphine) palladium (O). Conveniently an alcohol solvent may be used for the coupling reaction. The product compound of formula I may then be isolated and purified by conventional methods.

A third aspect of this invention is a liquid crystalline material, containing at least two components, at least one of which is a compound of formula I. This liquid crystalline material is preferably a nematic or cholesteric liquid crystalline material. Such materials may be used on electro-optic display devices such as watches and calculators etc, and also in thermochromic displays in which the colour or reflected light varies with temperature.

Compounds of formula I, in particular the preferred compounds referred to above, have a number of desirable properties which make them very useful components of liquid crystal materials. They often have higher nematic to isotropic (N-I) clearing point temperatures and lower melting points (C-N) than their unfluorinated counterparts. They generally have a high birefringence. They also generally show a higher solubility in commonly used liquid crystal materials than their unfluorinated counterparts. These advantages are not suggested by the prior art referred to above.

Suitable compounds for the other components of the liquid crystal material will be apparent to those skilled in the field, and will depend upon the properties such as dielectric anisotropy, birefringence, working temperature range etc., required in the material for the application for which the material is intended. Some types of suitable material are discussed briefly below.

Preferably as well as containing one or more formula I compounds the mixture contains one or more compounds of formula V:

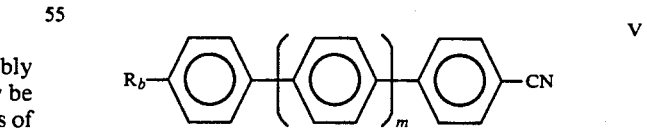

wherein R_b is alkyl or alkoxy, preferably containing 1 to 8 carbon atoms, and preferably straight chain, and wherein m is 0 or 1. Such compounds are included in the subject matter of GB 1433130.

Compounds of formula I have a positive dielectric anistrophy, and the material may for example contain other liquid crystalline compounds which have a positive dielectric anistrophy, for example as described in EP-A-0132377, particularly in FIG. 8 thereof and the related text.

The material may alternatively or also contain liquid crystalline compounds of low dielectric anistrophy, for example to form a mixture of intermediate dielectric anistrophy, or a thermochromic mixture. Some examples of such compounds are described in EP-A-0132377, particularly in FIG. 9 thereof and the related text.

The material may alternately or also contain liquid crystalline compounds having a high clearing point, for example to raise the N-I transition temperature. Some examples of such compounds are described in EP-A-0132377, particularly in FIG. 10 thereof and the related text.

To cause the material of this aspect of the invention to show a cholesteric (Ch) (or chiral nematic) phase the material must contain at least one compound containing an asymmetric carbon atom. This may be a chiral compound of formula I, or alternatively or also the material may for example contain one or more chiral compound of formula V above, e.g. (+) or (−) 4-(2-methylbutyl)-4'-cyano biphenyl or 4-(2-methylbutyloxy)-4'-cyano biphenyl.

The material may also contain one or more pleochroic dyes, for example the dyes described in EP-A-82300891.7.

The proportions of these components used in the material of this aspect of the invention will depend upon the intended application, and the material may usefully contain two or more compounds of formula I having different substituents or different dispositions of substituents on the terphenyl system.

The materials of this aspect of the invention may be used in any of the known forms of liquid crystal display device, for example a twisted nematic effect device, Freedericksz effect device, cholesteric memory mode device, cholesteric to nematic phase change effect device, dynamic scattering effect device, two frequency switching effect device, a "supertwist" effect device, or a thermometer using a thermochromic material. The method of construction and operation of such devices, and characteristics of a liquid crystal material suitable for use therein, are well known in the field. A liquid crystal display device which incorporates as its working fluid a material as described above, constitutes a fourth aspect of this invention.

DESCRIPTION OF THE PREFERRED EMBODIMENTS

The invention will now be described by way of example only with reference to FIG. 1 which shows the preparative route used in example 1 starting from 2-fluoro-4-bromo biphenyl to prepare a 4-alkyl-2'-fluoro-4"-cyano terphenyl, R in FIG. 1 being alkyl.

In these examples: C-N=solid crystal to nematic liquid crystal transition, N-I=nematic liquid crystal to isotropic liquid transition, $S_A$=smectic A liquid crystal phase. E7, E8 and K15 are Trade Marks of commercially available liquid crystal materials from BDH Ltd., Poole, GB and ZLI 1132 is a Trade Mark of a commercially available liquid crystal material from E. Merck GmbII, Darmstadt DE. The compositions of these materials have been published.

EXAMPLE 1

Preparation of compounds of general structure:

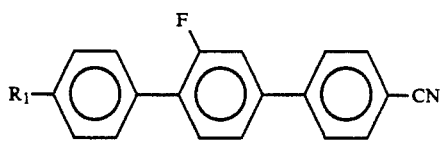

where $R_1$ is n-alkyl.

Step (i) Synthesis of ethyl 4-(4'-bromo-2'-fluorobiphenyl) ketone

To a suspension of aluminium chloride (40 g; 0.3 mol) in dichloromethan (100 ml) was slowly added, with stirring and ice bath cooling, a solution of propionyl chloride (20.9 g; 0.29 mol) and 2-fluoro-4-bromobiphenyl (62.5 g; 0.25 mol) in dichloromethane (10 ml). The mixture was stirred for 16 hrs at 20° C. and then carefully poured into ice/water (500 g), the organic material was extracted into dichloromethane (2×200 ml), washed with brine (2×100 ml) and dried over sodium sulphate. After evaporation of the dichloromethane, the solid was crystallised from two volumes of industrial spirits. Yield 62.3 g; 70%.

Step (ii) Synthesis of 4-bromo-2-fluoro-4'-propylbiphenyl

The product from step (i) 60 g; 0.196 mol) was dissolved in trifluoroacetic acid (100 ml) and triethyl silane (76 ml; 0.476 mol) was added dropwise while the temperature of the mixture was maintained at 10°-20° C. and then stirred for 16 hrs at 20° C. The reaction mixture was then poured into water (1 L) and extracted with ether (3×100 ml). After drying and evaporation of the ether, the product was distilled under high vacuum (1.5 mmHg). Yield 51.4 g; 90%.

Step (iii) Synthesis of 4'propyl-2-fluoro-4-biphenylboronic acid

The product from step (ii) (10 g; 0.034 mol) in tetrahydrofuran (35 ml) was added dropwise to a suspension of magnesium turnings (0.88 g) in tetrahydrofuran (5 ml). The mixture was warmed to 75° C. when the Grignard reaction started. Further of the bromo compound was slowly added and the external heat source removed, a gentle reflux being maintained. After complete addition, the mixture was heated for 30 mins under reflux and then cooled to 15° C. A dry nitrogen atmosphere was introduced and trimethyl borate (3.77 g; 0.0363 mol) was slowly added and the mixture stirred at 15°-20° C. for 16 hrs. A 20% soln of hydrochloric acid (50 ml) was slowly added, the organic layer was separated, and the aqueous layer extracted with ether (2×50 ml). The combined organic layers were washed with brine and dried over sodium sulphate. Upon evaporation of the solvents a yellow solid was obtained. Yield 8.7 g; 100%.

Step (iv) Synthesis of 4-propyl-2'-fluoro-4"'-cyano 1,1': 4',1"terphenyl

The crude product from step (iii) (8.7 g; 0.034 mol) 4-bromobenzonitrile (5.0 g; 0.0275 mol), tetrakis(triphenylphosphine) palladium (0.64 g) and methylated spirits (20 ml) were heated under reflux with vigorous stirring for 5 hrs. After cooling, the organic layer was separated, washed with water, dried over sodium sulphate and evaporated to dryness. The crude product was purified by column chromatography on silica gel followed by crystallisation from ethyl acetate. Yield 5.3 g; 51%.

The properties of some compounds prepared by the method of example 1, using an appropriate acyl chloride in step (i) are listed below:

EXAMPLE 3

The following difluorinated terphenyls were prepared using the method of example 1 and appropriately fluorinated starting materials;

TABLE 2

| Ref | $R_1$ | Structure | Liq. Crst. Transitions (°C.) | | | | | |
|-----|-------|-----------|------------------------------|---|---|---|---|---|
| 1a | $C_2H_5$ | | C—N | 109 | N—I | 201.5 | | |
| 1b | n-$C_3H_7$ | | C—N | 86.2 | N—I | 206 | | |
| 1c | n-$C_5H_{11}$ | R₁—⟨Ph⟩—⟨Ph-F⟩—⟨Ph⟩—CN | C—N | 97 | N—I | 189 | | |
| 1d | n-$C_4H_9O$ | | C—N | 88 | N—I | 228 | | |
| 1e | n-$C_7H_{15}O$ | | C—N | 89.5 | N—I | 203 | | |
| 1f | n-$C_8H_{17}O$ | | C—$S_A$ | 90 | $S_A$—N | 157.5 | N—I | 198.5 |

TABLE 4

| Ref | $R_1$ | Structure | Liq. Cryst. Transitions (°C.) | | | |
|-----|-------|-----------|-------------------------------|---|---|---|
| 3a | $C_2H_5$ | R₁—⟨Ph⟩—⟨Ph-F⟩—⟨Ph-F⟩—CN | C—N | 84.5 | N—I | 142.2 |
| 3b | n-$C_3H_7$ | R₁—⟨Ph⟩—⟨Ph-F⟩—⟨Ph-F⟩—CN | C—N | 102 (56) | N—I | 159 |
| 3c | n-$C_5H_{11}$ | R₁—⟨Ph⟩—⟨Ph⟩—⟨Ph-F,F⟩—CN | C—N | 102 | N—I | 121.5 | note:
( ) indicates temperature to which nematic N phase supercools.

EXAMPLE 2

Other compounds of formula I were prepared using a method analogous to that of example 1, as listed below:

Some comparative data for unfluorinated analogues of these compounds is listed below:

TABLE 3

| Ref | $R_1$ | Structure | Liq. Cryst. Transitions (°C.) | | | | | |
|-----|-------|-----------|-------------------------------|---|---|---|---|---|
| 2a | n-$C_3H_7$ | 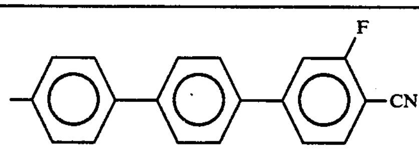 | C—N | 92 | N—I | 199 | | |
| 2b | n-$C_5H_{11}$ | R₁—⟨Ph⟩—⟨Ph⟩—⟨Ph-F⟩—CN | C—N | 85 (47) | N—I | 182 | | |
| 2c | n-$C_7H_{15}$ | | C—N | 86.3 | N—I | 169.2 | | |
| 2d | n-$C_9H_{19}$ | | C—$S_A$ | 72 | $S_A$—N | 139 | N—I | 159 |
| 2e | n-$C_3H_7$ | R₁—⟨Ph-F⟩—⟨Ph⟩—⟨Ph⟩—CN | C—N | 104 | N—I | 209.4 | | |
| 2f | n-$C_3H_7$ | R₁—⟨Ph⟩—⟨Ph-F⟩—⟨Ph⟩—CN | C—N | 88.1 | N—I | 205.4 | | |
| 2g | n-$C_5H_{11}$ | | C—N | 82 | N—I | 143 | | |

TABLE 4

| Ref | R₁ | Structure | Liq. Cryst. Transitions (°C.) |
|---|---|---|---|
| T9 | n-C₃H₇ | 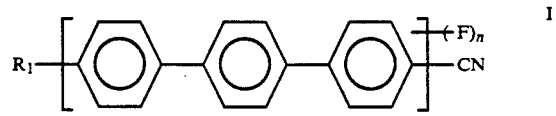 | C—N 182 N—I 275 |
| T15 | n-C₅H₁₁ | | C—N 130 N—I 239 |

From this data it can be seen that the melting point of the fluorinated compounds of the invention is substantially lower than those of the unfluorinated analogues, with little change in the breadth of the nematic phase.

EXAMPLE 4

Some data relating to liquid crystalline mixtures containing compounds of the invention is presented in tables 5 and 6 below. These compositions contain biphenyls and terphenyls of formula V. E7 having the composition:

n-C₅H₁₁—⟨O⟩—⟨O⟩—CN    39 wt % n-C₇H₁₅—⟨O⟩—⟨O⟩—CN    36 wt % n-C₈H₁₇O—⟨O⟩—⟨O⟩—CN    16 wt % n-C₅H₁₁—⟨O⟩—⟨O⟩—⟨O⟩—CN    9 wt% (= T15)

From tables 5 and 6 it can be seen that the fluorinated compounds of the invention have an improved birefringence and solubility in liquid crystals containing them relative to their unfluorinated analogues and that their incorporation in liquid crystal materials such as E8 can improve the N-I transition temperature and birefringence.

It was found to be difficult to freeze a 30 wt % solution of 1b in E7, and this factor allows the N-I and Δn of mixtures to be increased.

TABLE 5

| | Birefringence (Δn) | | Solubility in E7 | | Viscosity (cSt) at 20° C. in ZLI |
|---|---|---|---|---|---|
| | in K15 at 27° C. | in E7 at 20° C. | (wt %) at | | 1132 (η) |
| Ref | below N-I | below N-I | −10° C. | −20° C. | |
| T15 | 0.4138 | 0.330 | 9* | | 109 |
| 1b | 0.4531 | 0.377 | 23 | 20 | 228 |
| 1c | | 0.343 | 10 | | 195 |
| 2e | | | | 16 | |
| 2f | | | | 15 | |
| 2g | | | | 12 | |

(*in the biphenyls which make up E7)

TABLE 6

| | E8 | E8 + 20 wt % 1b |
|---|---|---|
| N-I (°C.) | 71 | 93 |
| η(cSt at 20° C.) | 54 | 75.7 |
| Δn (20° C.) | 0.2463 | 0.278 |

We claim:

1. Fluorinated 4″-cyanosubstituted terphenyl of the formula I:

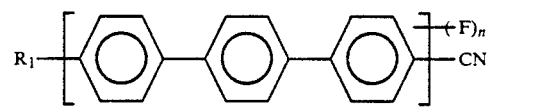

wherein $R_1$ is selected from the group consisting of alkenyl, R, RO, RCO and hydrogen, where R is alkyl or perfluoroalkyl containing 1 to 12 carbon atoms; n is 1, 2 or 3; and the fluorosubstituent may be in any of the available lateral substitution positions.

2. The compound according to claim 1 wherein $R_1$ is $C_2$-$C_9$ alkyl or alkoxy and n is 1 or 2.

3. The compound according to claim 2 being a 4-alkyl or alkoxy 2′-fluoro-4″-cyano terphenyl.

4. The compound according to claim 2 being a 4-alkyl or alkoxy 3″-fluoro-4″-cyano terphenyl.

5. The compound according to claim 2 being a 4-alkyl or alkoxy 2-fluoro-4″-cyano terphenyl.

6. The compound according to claim 2 being a 4-alkyl or alkoxy 3′-fluoro-4″-cyano terphenyl.

7. The compound according to claim 2 being a 4-alkyl or alkoxy 2′, 3″-difluoro-4″-cyano terphenyl.

8. The compound according to claim 2 being a 4-alkyl or alkoxy 2, 3″-difluoro-4″-cyano terphenyl.

9. The compound according to claim 2 being a 4-alkyl or alkoxy 3″, 5″-difluoro-4″-cyano terphenyl.

10. A liquid crystal composition containing at least two components, at least one being a fluorinated 4″-cyanosubstituted terphenyl of the formula I:

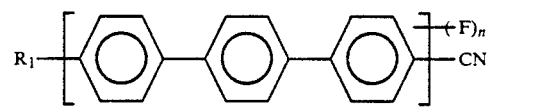

wherein $R_1$ is selected from the group consisting of alkenyl, R, RO, RCO and hydrogen, where R is alkyl or perfluoroalkyl containing 1 to 12 carbon atoms; n is 1, 2 or 3; and the fluorosubstituent may be in any of the available lateral substitution positions.

11. The liquid crystalline composition according to claim 10 wherein the composition also contains at least one compound of the formula V:

wherein $R_b$ is $C_1$-$C_8$ alkyl or alkoxy and m is 0 or 1.